US009572617B1

(12) United States Patent
Prado et al.

(10) Patent No.: US 9,572,617 B1
(45) Date of Patent: Feb. 21, 2017

(54) TORQUE LIMITING SURGICAL SCREW DRIVER

(71) Applicant: Xenco Medical, LLC, San Diego, CA (US)

(72) Inventors: Gustavo R. Prado, San Diego, CA (US); Ryan Woods, San Diego, CA (US)

(73) Assignee: XENCO MEDICAL LLC, San Diego, CA (US)

( * ) Notice: Subject to any disclaimer, the term of this patent is extended or adjusted under 35 U.S.C. 154(b) by 0 days.

(21) Appl. No.: 14/846,076

(22) Filed: Sep. 4, 2015

(51) Int. Cl.
*A61B 17/88* (2006.01)
*A61B 17/00* (2006.01)

(52) U.S. Cl.
CPC .... *A61B 17/8888* (2013.01); *A61B 2017/0023* (2013.01); *A61B 2017/0046* (2013.01); *A61B 2017/00407* (2013.01); *A61B 2017/00424* (2013.01)

(58) Field of Classification Search
CPC .................................................. A61B 17/8888
IPC .................................................. A61B 17/8888
See application file for complete search history.

(56) References Cited

U.S. PATENT DOCUMENTS

| 7,383,756 B1 | 6/2008 | Liu | |
|---|---|---|---|
| 2010/0275746 A1* | 11/2010 | Wengreen | A61B 17/8875 81/477 |

* cited by examiner

*Primary Examiner* — David Bates
*Assistant Examiner* — Olivia C Chang
(74) *Attorney, Agent, or Firm* — Wilson Sonsini Goodrich & Rosati

(57) ABSTRACT

Described herein are devices and methods for limiting the torque applied to surgical screw during a surgical procedure in which a surgical screw is passed into a vertebra, such as, for example, a spinal fusion procedure. A surgical screw driver is configured to prevent an excessive amount of torque from being delivered to the vertebrae through a surgical screw. When an excessive amount of torque is delivered to the handle of a surgical screw driver, it is prevented from being transmitted to the surgical screw and is thus not delivered to the vertebrae. Excessive force in the form of excessive torque transmitted to a vertebrae may cause a fracture along with possible mispositioning or displacement of a surgical screw.

13 Claims, 9 Drawing Sheets

TORQUE LIMITING SURGICAL SCREW DRIVER

BACKGROUND

Intervertebral disc disease and disc erosion as well as vertebral disease and vertebral deformity can cause severe back pain, and the typical pathophysiology of chronic back pain is a compression of a spinal nerve due to one of these spinal abnormalities.

When two vertebral bodies are separated by an eroded intervertebral disc, it can lead to a vertebral body collapsing onto the vertebral body directly below it. The collapse of the first vertebral body onto the second vertebral body deforms the vertebral anatomy, which can lead to a compression or pinching of a spinal nerve that can be exacerbated with motion.

The compression or pinching of a spinal nerve typically causes severe radiating pain down the distribution of the compressed or pinched nerve.

A typical surgical treatment for a compressed or pinched spinal nerve is a spinal fusion procedure. A spinal fusion procedure fuses two or more vertebrae together to eliminate the motion of these vertebrae, thus alleviating the nerve compression due to abnormal motion of the vertebrae.

A typical way to perform a spinal fusion procedure is by placing pedicle screws through the vertebral pedicles and into the vertebral bodies of two or more collapsed vertebra, and then attaching supporting bars to the pedicle screws. The supporting bars attached to the pedicle screws that are positioned within the vertebrae function similarly to scaffolding, connecting and fixing vertebrae together by fixing together pedicle screws embedded in the vertebrae.

A pedicle screw typically comprises a reticulating head referred to as a tulip. After the pedicle screw has been placed, a tulip may be used to align and secure a supporting bar that is coupled with that tulip. Once a desired position of a supporting bar is achieved a setscrew is used to fix the supporting bar to the tulip.

Torque applied to the pedicle screw and tulip setscrew to achieve proper placement and proper vertebral fixation is transferred to the vertebral pedicle and vertebral body. Too much torque applied to either the pedicle screw or tulip may fracture the vertebra through which a pedicle screw is placed or cause damage to the pedicle screw assembly.

Numerous other orthopedic procedures involve the placement of screws into bone, including, for example, bone fixation devices such as those used in long bone fracture reductions and fixations and in halos. Similar to vertebral fixation, too much torque applied when a screw is placed into a bone may cause fracture of the bone tissue or failure of the medical device.

SUMMARY

Described herein are methods and devices for limiting the torque applied to a screw or other similar device such as a bone tap being placed into bone as part of an orthopedic or neurosurgical procedure. Torque in various surgical procedures is typically applied by a hand-held instrument that is powered by a surgeon. A hand-held instrument may be similar to a traditional screw driver.

A torque limiting surgical screw driver and methods for limiting the torque that is applied to a screw being passed through a bone are beneficial, for example, in preventing bone fracture. In an embodiment, a torque limiting surgical screw driver may be configured to prevent the application of torque above a set threshold torque level to a surgical screw that may be used in, for example, an orthopedic or surgical procedure.

Traditional surgical screwdrivers and similar devices typically require recalibration following repeated steam sterilization undergone between surgical procedures. [Sadr et. al.] This poses a significant risk to patients, because it is difficult to track usage of such devices in the operating room, which makes recalibration difficult to do and as a result leaves recalibration schedules often unfulfilled. A low-cost, sterile-packaged, and disposable torque limiting surgical screw driver would be beneficial because such a screw driver would obviate the need for constant recalibration of re-used surgical screw drivers, which as explained are difficult to constantly recalibrate.

A low-cost, sterile-packaged, and disposable torque limiting surgical screw driver would offer significant benefits over currently available options. In order for a disposable device to be cost-effective, manufacturing methods such as plastic injection mold may be utilized. The challenge posed by injection-mold manufacturing is that molds that form instruments are expensive and hard to change once made. In addition, torque limiting devices usually need to be calibrated in order to precisely limit torque at a prescribed value. Described herein is an injection-moldable design and manufacturing method that is easily fine-tunable to the desired torque value.

Described herein is a torque limiting surgical screw driver, comprising a driver shaft having a proximal and a distal end, wherein the proximal end of the driver shaft comprises a first torque limiting element, and wherein the distal end of the driver shaft is configured to engage with a screw head used in a surgical procedure; a handle configured to couple with the proximal end of the driver shaft, wherein the handle comprises an opening configured to receive the proximal end of the driver shaft and a hollow interior continuous with the opening, and wherein the handle comprises a second torque limiting element within the hollow interior; wherein the second torque limiting element within the hollow interior of the handle is positioned to engage the first torque limiting element on the proximal end of the driver shaft when the proximal end of the driver shaft is coupled with the handle; and wherein the first and the second torque limiting elements are configured to disengage when a torque above a first threshold torque is applied to the handle when the handle is rotated in a clockwise direction. In an embodiment, the driver shaft has a length of about 30 cm. In an embodiment, the first torque limiting element comprises a leaflet comprising a first and a second portion, wherein the first portion is substantially rectangular and is positioned substantially perpendicular to the driver shaft, and wherein the second portion is substantially rectangular and further comprises a rounded lip at its distal end. In an embodiment, the proximal end of the driver shaft further comprises a third, a fourth, and a fifth torque limiting elements that are configured to respectively engage a sixth, a seventh, and an eighth torque limiting elements within the hollow interior of the handle. In an embodiment, the first torque limiting element comprises an elbow bend comprising an angle of 90 degrees or less. In an embodiment, the first torque limiting element comprises a polymer or plastic. In an embodiment, the handle is configured to reversibly couple with the driver shaft via a coupling mechanism. In an embodiment, the coupling mechanism comprises one or more threaded components. In an embodiment, one or more of the surgical screw driver, the driver shaft, and the handle are disposable. In an embodiment, the handle comprises a polymer or plastic. In an embodiment, the second torque limiting element is positioned so as to engage the first torque limiting element in a side by side fashion when the driver shaft is coupled with the handle. In an embodiment, the first torque limiting element is configured to bend in response to a pressure applied to the first torque limiting element by the second torque limiting element when the threshold torque is applied to the handle causing the first torque limiting element to disengage from the second torque limiting element. In an embodiment, the threshold torque comprises 90 inch pounds (10 N.m.) of torque. In an embodiment, the handle comprises a third torque limiting element within the hollow interior, and wherein the first torque limiting element on the handle is positioned between the second and third torque limiting elements when the handle is coupled with the driver shaft. In an embodiment, the first and the third torque limiting elements are configured to disengage when a torque above a second threshold torque is applied to the handle when the handle is rotated in a counter-clockwise direction.

Described herein is A method for limiting the amount of torque delivered to a surgical screw, comprising providing to a user a surgical screw driver with a torque limiting mechanism comprising a handle configured to couple with and rotate about a driver shaft, and further comprising two or more torque limiting elements that engage so that they together create a resistance to clockwise rotation of the handle about the driver shaft when the driver shaft is engaged with a surgical screw head of the surgical screw, until the user applies a torque above a first threshold torque to the handle in a clockwise direction that causes the two or more torque limiting elements to disengage so that the torque above the first threshold torque is not applied to the surgical screw head. In an embodiment, the driver shaft has a length of 30 cm. In an embodiment, the first torque limiting element comprises a leaflet comprising a first and a second portion, wherein the first portion is substantially rectangular and is positioned substantially perpendicular to the driver shaft, and wherein the second portion is substantially rectangular and further comprises a rounded lip at its distal end. In an embodiment, the two or more components comprise torque limiting elements, and wherein at least one torque limiting element is positioned on the driver shaft and at least one torque limiting element is positioned on the handle. In an embodiment, at least one of the one or more torque limiting elements comprises an elbow bend comprising an angle of 90. In an embodiment, at least one torque limiting element on the driver shaft comprises a polymer or plastic. In an embodiment, a handle is configured to reversibly couple with the surgical screw driver via a coupling mechanism. In an embodiment, a coupling mechanism comprises one or more threaded components. In an embodiment, one or more of the surgical screw driver, the driver shaft, and the handle are disposable. In an embodiment, the handle comprises a polymer or plastic. In an embodiment, the one or more torque limiting element on the handle is positioned so as to engage the first torque limiting element in a side by side fashion when the driver shaft is coupled with the handle. In an embodiment, at least one of the two or more torque limiting elements is configured to bend in response to a pressure applied to the at least one of the two or more torque limiting elements when the threshold torque is applied to the handle causing the at two or more torque limiting elements to disengage. In an embodiment, the threshold torque comprises 90 inch pounds of torque. In an embodiment, the method further comprises replacing one or more of the drive shaft and the handle. The method of claim 16, wherein the two or more torque limiting elements comprise a first and a second torque limiting elements, and wherein the first torque limiting element is positioned on the driver shaft and the second torque limiting element is positioned on the handle. In an embodiment, the method further comprises a third torque limiting element. In an embodiment, the third torque limiting element is configured to together create a resistance to counter-clockwise rotation of the handle about the driver shaft when the driver shaft is engaged with a surgical screw head of the surgical screw, until the user applies a torque above a second threshold torque to the handle in a counter-clockwise direction that causes the two or more torque limiting elements to disengage so that the torque above the threshold torque is not applied to the surgical screw head.

Described herein is a method for adjusting the amount of torque applied by a torque limiting surgical screw driver, comprising providing to a user a torque limiting surgical screw driver comprising a plurality of torque limiting elements configured to engage one another and a user controllable torque adjusting mechanism, wherein the user controllable torque adjusting mechanism is configured to cause one or more torque limiting elements of the plurality of torque limiting elements to reposition relative to one on or more torque limiting elements of the plurality of torque limiting elements so that a surface area over which the plurality of torque limiting elements engage is either increased or decreased. In an embodiment, the user controllable torque adjusting mechanism comprises a threaded piece. In an embodiment, the user controllable torque adjusting mechanism comprises a slideable switch. In an embodiment, the user controllable torque adjusting mechanism is configured to modify a resistance to a torque applied to the torque limiting surgical screw driver. In an embodiment, the resistance to a torque applied to the torque limiting surgical screw driver is modified by up to 10 inch pounds of torque.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the subject matter described herein are set forth with particularity in the appended claims. A better understanding of the features and advantages of the present subject matter will be obtained by reference to the following detailed description that sets forth illustrative embodiments, in which the principles of the subject matter described herein are utilized, and the accompanying drawings of which:

DETAILED DESCRIPTION

Figure 1A:
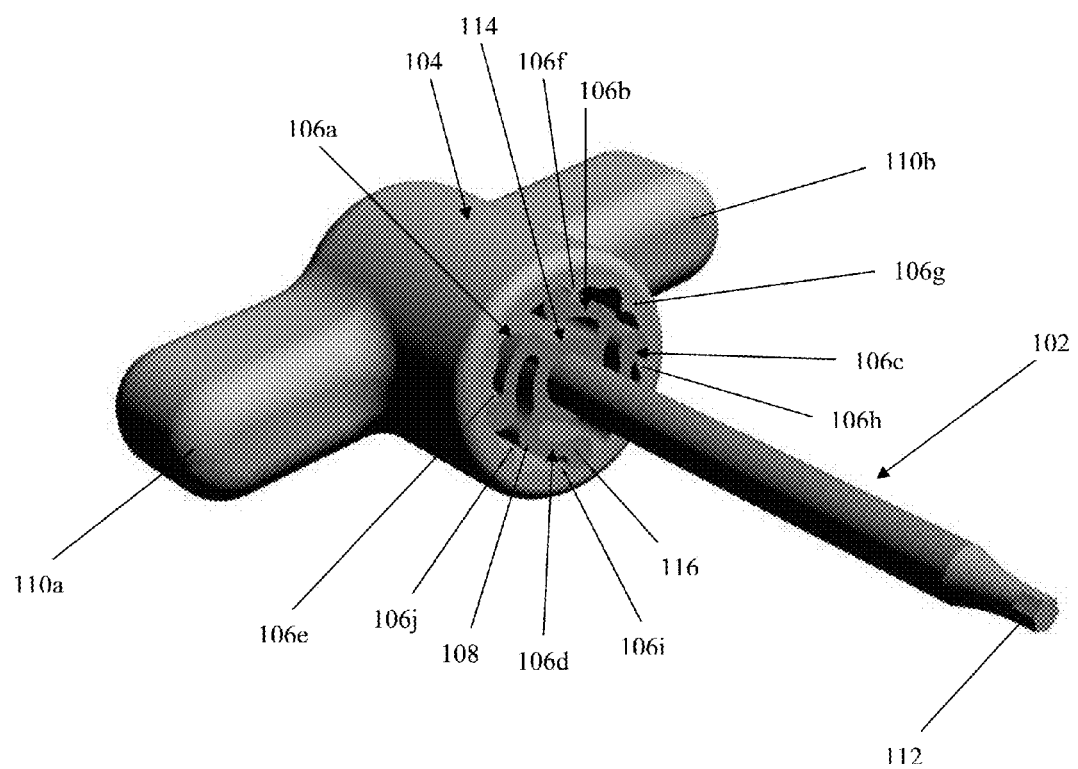
FIG. 1A shows an oblique view of an embodiment of a torque limiting surgical screw driver as described herein.

Described herein are devices, systems, and methods for limiting a torque applied to a screw being placed through a bone as part of an orthopedic or neurosurgical procedure. Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The term "subject" as used herein may refer to a human subject or any animal subject.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Described herein are methods and devices for limiting the amount of torque applied to a screw. For example, a pedicle screw used in a vertebral fixation surgery may fracture the vertebrae through which it is placed if too much torque is applied to the pedicle screw or the tulip while the pedicle screw or tulip is fixed in positon. It should be understood that the methods and devices described herein are also suitable for use in other orthopedic and neurosurgical procedures wherein a screw is placed in or through a bone. For example, the methods and devices described herein are not limited for use with spinal fixation procedures but are also useful with, for example, various internal and external bone fixation devices.

In an embodiment, a torque limiting surgical screw driver comprises a handle and a driver shaft.

Figure 6A:
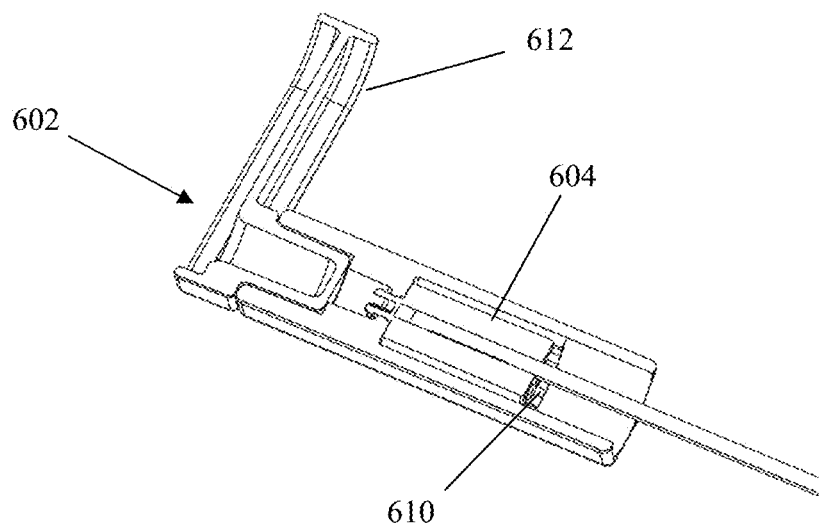
FIGS. 6A-6B show a cross-section of an embodiment of the torque limiting surgical screw driver as described herein.
Figure 6B:
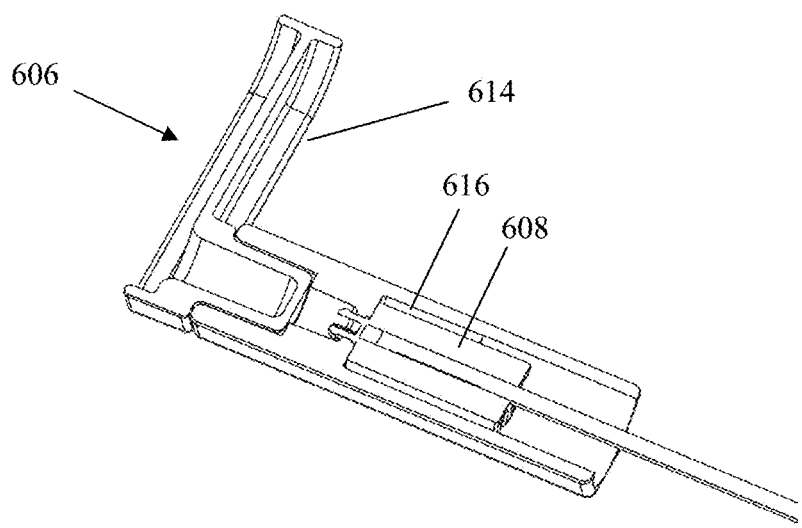

A handle may have various hand grips, wherein a grip comprises a portion of the handle that is configured to be grasped by a user, for example, during the use of the device by the user. In an embodiment, a handle comprises a tubular structure with a grip along its outside surface. In an embodiment, a handle has a T-grip that comprises two handle arms that are essentially perpendicular to the driver shaft. In an embodiment, a grip may comprise two or more handle arms that extend outward and away from the driver shaft. In an embodiment, a handle grip comprises a single arm. In an embodiment, one or more handle arms are reversibly coupleable with a handle. A handle arm may extend outward and away from the driver shaft for a length comprising about 4 cm. A handle arm may extend outward and away from the driver shaft for a length comprising about 3.5 cm. A handle arm may extend outward and away from the driver shaft for a length comprising about 3 cm. A handle arm may extend outward and away from the driver shaft for a length comprising about 2.5 cm. In an embodiment, a handle arm comprises a single piece (as shown in FIGS. 6A-6B) that projects away from the handle and may be, for example, positioned essentially perpendicular to the handle.

In an embodiment a handle comprises a metal such as, for example, steel or titanium. In an embodiment, a handle comprises a hard polymer or a plastic. Hard polymers or plastics may be injection molded.

In an embodiment, a handle has a hollow interior and an opening to receive a driver shaft. The hollow interior may be continuous with the opening for the driver shaft. A portion of the driver shaft may be positioned within the hollow interior of the handle.

In an embodiment, a driver shaft comprises a rod configured to engage a surgical screw, for example, a pedicle screw or a setscrew that couples with a tulip. A driver shaft may comprise metal, such as, for example, steel or titanium, a polymer, or a hard plastic, wherein a hard polymer or plastic may be machine molded. A pedicle screw is a screw configured to be passed through a pedicle of a vertebra and into the vertebral body to fix two or more vertebrae together. A, tulip as is it is known in the art, comprises an articulating head of a pedicle screw that is configured to receive and fasten a rod. A tulip may be fixed in place with a setscrew that couples with the head of a tulip, and, for example, fixes a rod against a saddle within the tulip.

A distal end of a driver shaft may be configured to engage directly with a surgical screw head, a pedicle screw head, a tulip, or a tulip screw head so that the driver shaft may transfer an applied torque to any of the pedicle screws, tulip, or tulip screws as would a common screw driver.

A proximal end of a driver shaft is configured to couple with a handle as described herein.

In an embodiment, a length of a driver shaft may be configured to stabilize the driver when engaged with one of the pedicle screw, tulip, or setscrew while allowing for efficient delivery of torque. That is, typically, there exists a length or range of lengths of a driver shaft at which the driver is stable while engaged to a screw and torque is efficiently delivered to the screw. For example, a driver shaft that is too long is likely less stable when engaged with a screw, and, for example, a driver shaft that is too short will likely lead to less efficient delivery of torque to the screw. In an embodiment, a driver shaft may have a length of 40 cm.

In an embodiment, a driver shaft may have a length of 39 cm. In an embodiment, a driver shaft may have a length of 38 cm. In an embodiment, a driver shaft may have a length of 37 cm. In an embodiment, a driver shaft may have a length of 36 cm. In an embodiment, a driver shaft may have a length of 35 cm. In an embodiment, a driver shaft may have a length of 34 cm. In an embodiment, a driver shaft may have a length of 33 cm. In an embodiment, a driver shaft may have a length of 32 cm. In an embodiment, a driver shaft may have a length of 31 cm. In an embodiment, a driver shaft may have a length of 30 cm. In an embodiment, a driver shaft may have a length of 29 cm. In an embodiment, a driver shaft may have a length of 28 cm. In an embodiment, a driver shaft may have a length of 27 cm. In an embodiment, a driver shaft may have a length of 26 cm. In an embodiment, a driver shaft may have a length of 25 cm. In an embodiment, a driver shaft may have a length of 24 cm. In an embodiment, a driver shaft may have a length of 23 cm. In an embodiment, a driver shaft may have a length of 22 cm. In an embodiment, a driver shaft may have a length of 21 cm. In an embodiment, a driver shaft may have a length of 20 cm. In an embodiment, a driver shaft may have a length of 19 cm. In an embodiment, a driver shaft may have a length of 18 cm. In an embodiment, a driver shaft may have a length of 17 cm. In an embodiment, a driver shaft may have a length of 16 cm. In an embodiment, a driver shaft may have a length of 15 cm. In an embodiment, a driver shaft may have a length of 14 cm. In an embodiment, a driver shaft may have a length of 13 cm. In an embodiment, a driver shaft may have a length of 12 cm. In an embodiment, a driver shaft may have a length of 11 cm. In an embodiment, a driver shaft may have a length of 10 cm. In an embodiment, a driver shaft may have a length of 9 cm. In an embodiment, a driver shaft may have a length of 8 cm. In an embodiment, a driver shaft may have a length of 7 cm. In an embodiment, a driver shaft may have a length of 6 cm. In an embodiment, a driver shaft may have a length of 5 cm.

In an embodiment, a ratio of the length of a handle along its grip relative to the length of the driver shaft may be configured to stabilize the driver when engaged with one of the pedicle screw, tulip, or tulip screw while allowing for efficient delivery of torque. That is, typically there exists a ratio of the length of a handle grip to the length of a driver shaft at which the driver is stable while engaged to a screw and torque is efficiently delivered to the screw. In an embodiment, a ratio of the length of the handle relative to the length of the driver shaft may be, for example, about 1:7. In an embodiment, a ratio of the length of the handle relative to the length of the driver shaft may be, for example, about 1:6. In an embodiment, a ratio of the length of the handle relative to the length of the driver shaft may be, for example, about 1:5. In an embodiment, a ratio of the length of the handle relative to the length of the driver shaft may be, for example, about 1:4. In an embodiment, a ratio of the length of the handle relative to the length of the driver shaft may be, for example, about 1:3. In an embodiment, a ratio of the length of the handle relative to the length of the driver shaft may be, for example, about 1:2. In an embodiment, a ratio of the length of the handle relative to the length of the driver shaft may be, for example, about 1:1.

In an embodiment, surgical screw driver comprises a handle rotatably coupled with a driver shaft. That is, in this embodiment, the handle is configured to rotate about the driver shaft. The handle may be fixed to the driver shaft, by for example, a screw or pin passing through the handle into the driver shaft in the axis of rotation of the handle. Alternatively or additionally, the handle may be configured to reversibly couple with the driver shaft. In an embodiment, the handle and driver shaft may be configured to reversibly couple so that a handle may be used with multiple interchangeable driver shafts, and a driver shaft may be used with multiple interchangeable handles.

In an embodiment, a handle may rotatably couple with a driver shaft without attaching directly to the driver shaft. In this embodiment, a proximal end of a driver shaft may be wider than the rest of the driver shaft. In this embodiment, a handle may be coupled to the wide proximal end of the driver shift by being fitted around the wide proximal end of the driver shaft. In this embodiment, when the handle is positioned around the wide proximal end of the driver shaft, the wide proximal end of the driver shaft is positioned within a hollow interior portion of the handle. The handle further comprises an opening that is large enough in diameter for the narrow portion of the shaft to fit through but not wide enough for the wide proximal portion of the driver shaft to fit through. Thus, in this embodiment, the wide proximal portion of the drive shaft is unable to slide out through the opening in the handle. In an embodiment, a handle comprises two or more pieces and the handle is thus fitted around a wide proximal portion of a driver shaft by fitting the two or more pieces together that form the handle around the wide proximal portion of the driver shaft. In an embodiment, two or more pieces that form a handle may be interlocking. In an embodiment, two or more pieces that form a handle may be reversibly couplable so that a handle may, for example, be coupled with different driver shafts.

In an embodiment, a surgical screw driver comprises a torque limiting mechanism. In an embodiment, a torque limiting mechanism prevents the transmission of torque to a screw when a torque above a certain threshold is applied by a user to a torque limiting surgical screw driver. In an embodiment, a torque limiting mechanism may comprise one or more torque limiting elements positioned on a driver shaft and one or more corresponding torque limiting elements positioned on the handle. In an embodiment, one or more torque limiting element positioned on a handle are positioned either inside the interior of the handle, on the opening of the handle, or positioned on both the opening and within the hollow portion of the handle. In an embodiment, when the torque limiting element of the driver shaft and the torque limiting element of the handle are not coupled together or otherwise engaged, the handle is freely rotatable around the driver shaft. When the torque limiting elements are coupled together or otherwise engaged, the handle is prevented from rotating, and a torque that is applied to the handle is transferred to the driver shaft, and may in turn be transferred to a surgical screw such as, for example, a pedicle screw, tulip, or tulip screw.

In an embodiment, a torque limiting mechanism decouples or disengages one or more torque limiting elements once a torque above a certain limit is delivered to the handle by a user, so that the handle is freed to rotate around the driver shaft and does not transmit torque to the driver shaft. The torque limiting mechanism may be configured, so that it decouples or disengages one or more torque limiting elements when a torque is delivered to the handle that would transmit a torque to the pedicle screw, tulip, or tulip screw that exceeds a torque that is safe to deliver to a pedicle screw, tulip, or tulip screw. Thus, the torque liming mechanism may be configured to prevent excess torque from being delivered through the driver to a pedicle, tulip, or tulip screw by decoupling once an excess torque is delivered.

In an embodiment, a coupling mechanism comprises one or more torque limiting elements positioned on the handle and one or more torque limiting elements positioned on the proximal end of the driver shaft. The torque limiting element on the handle may be inside of the handle, along the handle opening, or along both the handle interior and opening. The torque limiting elements may, for example, comprise the same material as either the handle or driver shaft or a different material. In an embodiment, one or more torque limiting elements are shaped so that they couple or engage one another by pressing against each other. That is, in an embodiment, a proximal end of a driver shaft extends into a hollow interior of a handle so that torque limiting elements on the proximal portion of the driver shaft are positioned side by side against torque limiting elements on and/or inside the handle. When a torque is applied to the handle, the side-by-side torque limiting elements are pressed against each other and resist rotation of the handle around the driver shaft. When, however, a torque is applied above a certain threshold of force either the torque limiting element on the driver shaft, the torque limiting element on and/or inside the handle, or both the torque limiting element on and/or inside the handle and the torque limiting element on the driver shaft may become distorted so that the two torque limiting elements are no longer pressed against each other but instead move by each other, thusly becoming decoupled or disengaged.

In an embodiment, a torque limiting element comprises a rectangular shape and protrudes out similar to a wing or flap. In an embodiment, a torque limiting element comprises a globular shape. In an embodiment, a torque limiting element comprises a hook. It should be understand that numerous shapes and structures are suitable for use with the devices and methods described herein.

In an embodiment, a torque limiting element is L-shaped. An L-shaped torque limiting element may be essentially rectangular in shape and have a bend along its protruding length that forms and L-shape. It should be understood that the point along the length of the torque limiting element wherein the bend is positioned may vary to any degree and still be suitable for the devices and methods described herein. Likewise, the angle of the bend may vary and may, for example, be about 90 degrees. The angle of the bend of the L-shaped torque limiting element may, for example, be any angle less than 90 degrees. The angle of the L-shaped torque limiting element may, for example, be any angle greater than 90 degrees.

In an embodiment multiple torque limiting elements are positioned on a proximal end of a driver shaft and are all L-shaped. The driver shaft couples with a handle that has a matching number of torque limiting elements that are configured to couple or engage with the L-shaped torque limiting elements on the proximal end of the driver shaft. When the L-shaped torque limiting elements on the proximal end of the driver shaft couple or engage with the torque limiting elements on the handle the ends of the L-shaped torque limiting elements rest against the torque limiting elements of the handle. When the driver shaft is engaged with a pedicle screw, tulip, or tulip screw and a torque is applied to the handle that is below a certain threshold, the L-shaped torque limiting elements press against the handle torque limiting elements so that the torque applied to the handle is transmitted to the driver shaft and then to the pedicle, tulip, or tulip screw. In an embodiment, when the torque applied to the handle exceeds the certain threshold, the L-shaped torque limiting elements distort so that the angle at the elbow increases straightening the multiple L-shaped torque limiting elements and allowing them to move over and around the handle torque limiting elements, so that the handle rotates freely over a distance between two adjacent torque limiting elements. One the handle rotates freely, the excess torque that was applied cannot be transmitted.

In an embodiment, a coupling mechanism comprises interlocking torque limiting elements. In an embodiment, interlocking torque limiting elements comprise one or more magnets. That is, a locking mechanism may comprise two magnets, or one magnet and one metal piece that is configured to magnetically couple to the magnet. In an embodiment, interlocking torque limiting elements slidably interlock, and may, for example, comprise a torque limiting element having a male torque limiting element that slidably couples with a torque limiting element having a female torque limiting element. An interlocking torque limiting element may be configured to decouple when a torque above a certain threshold is applied to the handle as described herein.

In an embodiment, a coupling mechanism may comprise two or more torque limiting elements. A coupling mechanism may, for example, couple together torque limiting elements that are not in a one to one correspondence with each other. For example, a single torque limiting element on and/or inside the handle may couple or engage simultaneously with two or more torque limiting elements on the driver shaft.

In an embodiment, a plurality of torque limiting elements on and/or inside a handle are in a one to one relationship with a plurality of torque limiting elements on a driver shaft. In an embodiment, a plurality of torque limiting elements on and/or inside a handle are not in a one to one relationship with a plurality of torque limiting elements on a driver shaft.

In an embodiment, the type of torque limiting element on and/or inside the handle may be of the same type as the torque limiting element on the driver shaft. For example, a rectangular shaped torque limiting element may couple or engage with a rectangular shaped torque limiting element on and/or inside the handle. In an embodiment, the type of torque limiting element on and/or inside the handle may not be of the same type as the torque limiting element on the driver shaft. For example, a rectangular shaped torque limiting element on and/or inside the handle may couple or engage with a globular shaped torque limiting element on the proximal end of the driver shaft. Likewise, a combination of different types of coupling mechanisms may be used. For example, a coupling mechanism comprising two magnets may be used together with a coupling mechanism comprising two hooks.

Typically, one or more torque limiting mechanisms may be used with any of the devices and methods described herein each comprising of one or more torque limiting elements. Typically, the, for example, shape, configuration, material, and number of torque limiting elements are selected to apply a certain resistance that is overcome by a torque greater than the pre-determined resistance that is applied. Other factors that affect torque including, for example, the shape and resistance to rotation of the handle are typically accounted for as well when configuring the one or more torque limiting elements of the one or more torque limiting mechanisms.

In an embodiment, a torque limiting surgical screw driver may be configured to prevent the application of a torque above a specific set threshold. In an embodiment, a specific set threshold torque is determined by the properties of the materials chosen to use for make the torque limiting elements. In an embodiment, a specific set threshold torque is determined by the number of torque limiting elements. In an embodiment, a specific set threshold torque is determined by size of the torque limiting elements. In an embodiment, a specific set threshold torque is determined by the physical properties of torque limiting elements. In an embodiment, a specific set threshold torque is determined and set by a user. In an embodiment, a specific set threshold torque comprises 115 inch pounds. In an embodiment, a specific set threshold torque comprises 110 inch pounds. In an embodiment, a specific set threshold torque comprises 105 inch pounds. In an embodiment, a specific set threshold torque comprises 100 inch pounds. In an embodiment, a specific set threshold torque comprises 95 inch pounds. In an embodiment, a specific set threshold torque comprises 90 inch pounds. In an embodiment, a specific set threshold torque comprises 85 inch pounds. In an embodiment, a specific set threshold torque comprises 80 inch pounds. In an embodiment, a specific set threshold torque comprises 75 inch pounds. In an embodiment, a specific set threshold torque comprises 70 inch pounds.

In an embodiment, a torque limiting surgical screw driver is configured so that a set torque is manually determined or adjusted by a user. In an embodiment, one or more torque limiting elements on either a handle or a driver shaft may be repositioned so that more or less of the surface area of the one or more torque limiting elements contact one another when the respective elements engage. For example, in an embodiment, wherein a torque limiting element on a handle engages with a torque limiting element on a driver shaft in, for example, a side-by-side fashion, a decrease in the amount of surface area over which the two torque limiting elements contact will decrease the amount of torque required to cause the two torque limiting elements to disengage. For example, in an embodiment, wherein a torque limiting element on a handle engages with a torque limiting element on a driver shaft in, for example, a side-by-side fashion, an increase in the amount of surface area over which the two torque limiting elements contact will increase the amount of torque required to cause the two torque limiting elements to disengage. That is, an increase in the amount of surface area over which two or more torque limiting elements engage with each other will typically increase the amount of torque that is necessary to apply in order to disengage the two or more torque limiting elements. A decrease in the amount of surface area over which two or more torque limiting elements engage with each other will typically decrease the amount of torque that is necessary to apply in order to disengage the two or more torque limiting elements. In an embodiment, an amount of surface area over which two or more torque limiting elements engage may be adjusted by a user by a mechanism that, for example, repositions one or more torque limiting elements relative to a one or more other torque limiting elements. For example, in an embodiment, a torque limiting surgical screw driver comprises a driver shaft that is configured to move in and out relative to an opening within a handle. That is, in an embodiment, a mechanism is configured to controllably cause a driver shaft to move in and out relative to a handle to which the driver shaft is coupled. In an embodiment, a manual control is positioned on the handle that when activated by a user causes the driver shaft to either advance out of the interior of the handle or advance in towards the interior of the handle so that one or more torque limiting elements positioned on the driver shaft are repositioned relative to one or more torque limiting elements positioned on the handle. In an embodiment, a user controllable torque adjusting mechanism comprises a threaded piece functionally coupled to the driver shaft. When the threaded piece is turned by the user the driver shaft is either advanced in or out of the interior of the handle. In an embodiment, the threaded piece itself is advanced or withdrawn relative to the driver shaft when it is turned. In an embodiment, the threaded piece is positioned on top of the handle. In an embodiment, a user controllable torque adjusting mechanism comprises a slideable switch that is functionally coupled to the driver shaft. In an embodiment, when a slideable switch is slid up or down on a track it causes a driver shaft to advance in or out relative to an interior of a handle to which it is coupled. In an embodiment, a user controllable torque adjusting mechanism is configured to cause the repositioning of one or more torque limiting elements in a fashion that causes a predictable adjustment in the amount of torque required to disengage two or more torque limiting elements. For example in an embodiment, a user controllable torque adjusting mechanism is configured to modify the amount of torque necessary to disengage two or more torque limiting elements by up to 30 or more inch pounds. For example in an embodiment, a user controllable torque adjusting mechanism is configured to modify the amount of torque necessary to disengage two or more torque limiting elements by up to 20 or more inch pounds. For example in an embodiment, a user controllable torque adjusting mechanism is configured to modify the amount of torque necessary to disengage two or more torque limiting elements by up to 15 or more inch pounds. For example in an embodiment, a user controllable torque adjusting mechanism is configured to modify the amount of torque necessary to disengage two or more torque limiting elements by up to 14 or more inch pounds. For example in an embodiment, a user controllable torque adjusting mechanism is configured to modify the amount of torque necessary to disengage two or more torque limiting elements by up to 13 or more inch pounds. For example in an embodiment, a user controllable torque adjusting mechanism is configured to modify the amount of torque necessary to disengage two or more torque limiting elements by up to 12 or more inch pounds. For example in an embodiment, a user controllable torque adjusting mechanism is configured to modify the amount of torque necessary to disengage two or more torque limiting elements by up to 11 or more inch pounds. For example in an embodiment, a user controllable torque adjusting mechanism is configured to modify the amount of torque necessary to disengage two or more torque limiting elements by up to 10 or more inch pounds. For example in an embodiment, a user controllable torque adjusting mechanism is configured to modify the amount of torque necessary to disengage two or more torque limiting elements by up to 9 or more inch pounds. For example in an embodiment, a user controllable torque adjusting mechanism is configured to modify the amount of torque necessary to disengage two or more torque limiting elements by up to 8 or more inch pounds. For example in an embodiment, a user controllable torque adjusting mechanism is configured to modify the amount of torque necessary to disengage two or more torque limiting elements by up to 7 or more inch pounds. For example in an embodiment, a user controllable torque adjusting mechanism is configured to modify the amount of torque necessary to disengage two or more torque limiting elements by up to 6 or more inch pounds. For example in an embodiment, a user controllable torque adjusting mechanism is configured to modify the amount of torque necessary to disengage two or more torque limiting elements by up to 5 or more inch pounds. For example in an embodiment, a user controllable torque adjusting mechanism is configured to modify the amount of torque necessary to disengage two or more torque limiting elements by up to 4 or more inch pounds. For example in an embodiment, a user controllable torque adjusting mechanism is configured to modify the amount of torque necessary to disengage two or more torque limiting elements by up to 3 or more inch pounds. For example in an embodiment, a user controllable torque adjusting mechanism is configured to modify the amount of torque necessary to disengage two or more torque limiting elements by up to 2 or more inch pounds. For example in an embodiment, a user controllable torque adjusting mechanism is configured to modify the amount of torque necessary to disengage two or more torque limiting elements by up to 1 or more inch pounds. In an embodiment, a user controllable torque adjusting mechanism is configured to modify the amount of torque necessary to disengage two or more torque limiting elements by increments of 5 or more inch pounds. In an embodiment, a user controllable torque adjusting mechanism is configured to modify the amount of torque necessary to disengage two or more torque limiting elements by increments of 2 or more inch pounds. In an embodiment, a user controllable torque adjusting mechanism is configured to modify the amount of torque necessary to disengage two or more torque limiting elements by increments of 1 or more inch pounds.

FIG. 1A shows an oblique view of an embodiment of a torque limiting surgical screw driver. In the shown embodiment, a torque limiting surgical screw driver comprises a driver shaft 102 which is rotatably coupled to a handle 104. A driver shaft 102 may comprise a distal portion that comprises a driver shaft tip 112 configured to engage with a screw, and a proximal portion that comprises four torque limiting elements 106a, 106b, 106c, 106d. In this embodiment, torque limiting elements 106a, 106b, 106c, and 106d comprise leaflets that project out of a torque limiting unit 114 which in turn couples with the driver shaft 102. In this embodiment, the torque limiting unit 114 comprises a hole through which the driver shaft 102 passes. Having torque limiting elements 106a, 106b, 106c, and 106d comprise a torque limiting unit 114 which couples with the driver shaft 102 is advantageous, for example, in that the torque limiting unit 114 and torque limiting elements 106a, 106b, 106c, and 106d may comprise a different material than the driver shaft. In an embodiment, manufacture of the torque limiting surgical screw driver described herein comprises over-molding the torque limiting unit 114 around the driver shaft 102, thus permanently binding together the driver shaft 102 and the torque limiting unit 114. Torque limiting elements 106a, 106b, 106c, and 106d may comprise a relatively bendable material such as a polymer and the driver shaft 102 may comprise a harder material such as a metal, for example, steel. In an embodiment (not shown), torque limiting elements 106a, 106b, 106c, and 106d are attached directly to the driver shaft 102 and project directly from the driver shaft 102. In the shown embodiment, the torque limiting unit 114 is affixed to the driver shaft 102, so that the torque limiting unit 114 and attached torque limiting elements 106a, 106b, 106c, and 106d do not rotate around the driver shaft 102. In the shown embodiment, each of the torque limiting elements 106a, 106b, 106c, and 106d positioned on the driver shaft 102 comprise an elbow 108. In an embodiment, each of the torque limiting elements 106a, 106b, 106c, and 106d are configured to bend at an elbow 108. In an embodiment, each of the torque limiting elements 106a, 106b, 106c, and 106d on the driver shaft 102 comprise an edge 116 that is rounded and is configured to engage a torque limiting element on the handle 104. In an embodiment, edge 116 functions similar to a cam follower, wherein when torque is applied to a torque limiting element on a handle, the torque limiting element on the handle functions similar to a cam leader, in that it is configured to rotationally displace edge 116 similar to a displacement of a cam follower by a cam leader. In an embodiment, the torque limiting elements 106a, 106b, 106c, and 106d on the driver shaft 102 extend along at least a portion of the interior of the handle 104. In an embodiment, the torque limiting elements 106a, 106b, 106c, and 106d on the driver shaft 102 extend along the entire interior of the handle 104. A handle 104 may comprise a T-grip which comprises two handle arms 110a and 110b. A handle may further comprise eight torque limiting elements (only six are shown in FIG. 1A) 106e, 106f, 106g, 106h, 106i, 106j that are positioned along the length of at least a portion of the hollow interior portion of the handle 104. In an embodiment, the eight torque limiting elements (only six are shown in FIG. 1A) 106e, 106f, 106g, 106h, 106i, 106j are extend along the entire length of the interior of the handle 104. Each of the torque limiting elements on the handle 106e, 106f, 106g, 106h, 106i, 106j (two not shown) is separated by a track. The torque limiting elements 106a, 106b, 106c, and 106d on the driver shaft are configured to move along the track between the torque limiting elements on the handle 106e, 106f, 106g, 106h, 106i, 106j when the handle 104 is rotated about the driver shaft 102. Torque limiting elements 106e, 106f, 106g, 106h, 106i, 106j on the hollow interior of the handle engage or couple with the torque limiting elements 106a, 106b, 106c, and 106d on the driver shaft. Any of the torque limiting elements 106a, 106b, 106c, and 106d on the driver shaft may couple or engage with any of the torque limiting elements 106e, 106f, 106g, 106h, 106i, 106j (and the two not shown) on the hollow interior of the handle. When, for example, a torque limiting element 106a on the driver shaft 102 engages or couples with a torque limiting element 106e on the handle 104, clockwise rotation of the handle 104 around the driver shaft 102 is resisted by the engagement or coupling of the torque limiting elements 106a and 106e. In this embodiment, torque limiting element 106a comprises an L-shaped torque limiting element that protrudes outward from the driver shaft and torque limiting element 106e comprises a ridge-like torque limiting element along the inside of the handle 104, and the tip of torque limiting element 106a presses against the ridge-like torque limiting torque limiting element 106e when a torque is applied to the handle 104 and the driver shaft 102 is held. The driver shaft 102 may be held by, for example, the driver shaft tip 112 engaging with the head of a screw that is being advanced through bone. When a torque is applied to handle 104, and the driver shaft 102 is engaged with a screw head, the torque may be transferred directly to the driver shaft 102 from the handle 104. The torque delivered to the driver shaft 102 from the handle may then be transferred from the driver shaft 102 to the screw head to, for example, drive the screw into a bone. As long as the torque applied to the handle does not exceed the resistance created by the engaged torque limiting elements on the driver shaft and handle, the torque applied to a handle 102 will be transferred to the driver shaft 104. When the torque applied to a handle 102 exceeds the resistance created by the engaged torque limiting elements on the driver shaft and handle, the torque limiting elements will disengage. When the torque limiting elements on the driver shaft 102 and handle 104 disengage there is no longer any resistance to rotation of the handle 102 applied by the torque limiting elements, and the handle 104 rotates around the driver shaft 102 in response to the applied torque. When the handle 104 rotates around the driver shaft 102, no torque is transferred to the driver shaft 104, and no torque is transferred to the screw head. That is, in this embodiment, when torque limiting elements on the handle 104 and torque limiting elements on the driver shaft 102 disengage, torque is not transferred to a screw head by the torque limiting surgical screw driver. In this embodiment, torque applied to a handle 104 in a clockwise direction it causes four of the torque limiting elements 106e, 106f, 106g, 106h, 106i, 106j (and the two not shown) on the handle 104 to correspondingly engage the four torque limiting elements 106a, 106b, 106c, and 106d on the driver shaft. In this embodiment, when a torque that is applied to a handle 104 in a clockwise direction is sufficiently large it causes four of the torque limiting elements 106e, 106f, 106g, 106h, 106i, 106j (and the two not shown) on the handle 104 to correspondingly disengage from the four torque limiting elements 106a, 106b, 106c, and 106d on the driver shaft to which they had been previously engaged. In an embodiment, torque limiting elements on the handle 104 and torque limiting elements on the driver shaft 102 disengage, for example, when a clockwise torque applied to the handle 104 causes the torque limiting elements on the handle 104 to press against the torque limiting elements on the driver shaft 102 with sufficient force to cause the torque limiting elements on the driver shaft to bend at their respective elbows. As the torque limiting elements become progressively more bent at their respective elbows due to the pressure applied to them by the torque limiting elements on the handle, the amount of resistance to rotation of the handle 104 around the driver shaft 102 decreases. When the resistance to rotation sufficiently decreases due to bending of the torque limiting elements on the driver shaft, the torque limiting elements on the handle 104 rotate past the torque limiting elements on the driver shaft 102 such that the torque limiting elements become disengaged and the handle 104 rotates about the driver shaft 102, until the torque limiting elements on the handles each respectively encounter another torque limiting element on the driver shaft 102.

Figure 1B:
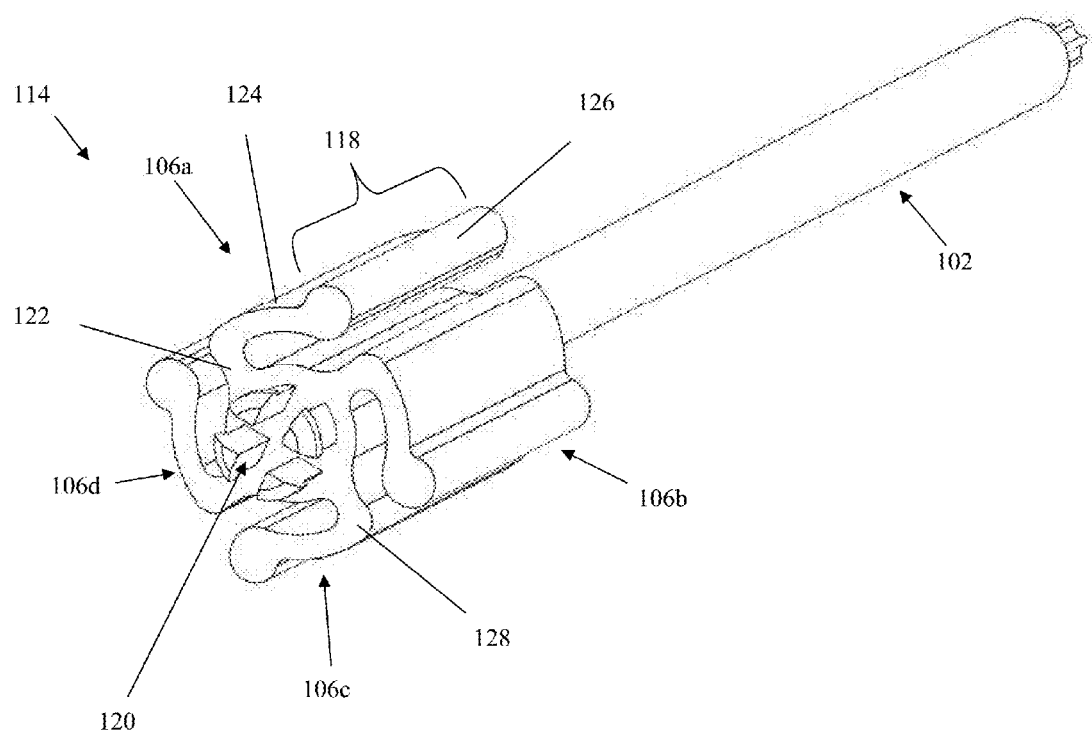
FIG. 1B shows an embodiment of a driver shaft and torque limiting unit as described herein.

FIG. 1B shows an embodiment of a driver shaft 102 and torque limiting unit 114 that are not coupled with a handle. In an embodiment, a torque limiting unit 114 comprises four leaflets 106a, 106b, 106c, and 106d. In an embodiment, a torque limiting unit 114 is molded around a driver shaft 102. In an embodiment (not shown), the four leaflets 106a, 106b, 106c, and 106d may be individually molded onto a driver shaft 102 and not configured as part of a torque limiting unit 114. In an embodiment, the four leaflets 106a, 106b, 106c, and 106d may be continuous with a driver shaft 102. In an embodiment, the four leaflets 106a, 106b, 106c, and 106d may comprise the same material as the drier shaft 102. In an embodiment, the torque limiting unit 114 and four leaflets 106a, 106b, 106c, and 106d may comprise a polymer and the driver shaft 102 may comprise a metal. In an embodiment, protrusions 120 are configured to couple a driver shaft to a handle. In an embodiment, a leaflet length 118 may be set for one or more leaflets 106a, 106b, 106c, and 106d during the manufacturing process in order to provide a particular resistance to a torque. For example, typically, the longer the leaflet length 118 the greater will be the resistance provided by the leaflet to an applied torque, and the shorter the length 118 the lower greater will be the resistance provided by the leaflet to an applied torque. The relationship of a leaflet length 118 together with, for example, the material and shape of a leaflet, to a resistance to particular torque is predictable, so that the leaflets may be manufactured specifically to resist a specific torque. As described, in an embodiment, the surface area of a leaflet engaged with a torque limiting element on a handle (not shown in FIG. 1B) may be manually adjusted by a user to modify the resistance to torque of leaflets as well.

In an embodiment, a leaflet comprises a first portion 122 that is connected to and continuous with a second portion 124. In an embodiment, a first portion 122 is positioned substantially perpendicular to the driver shaft 102. In an embodiment, the first portion 122 is directly attached to a torque limiting unit 114. In an embodiment, the first portion 122 is directly attached to a driver shaft 102. In an embodiment, the first portion 122 is substantially rectangular. In an embodiment, the second portion 124 is substantially rectangular. In an embodiment, the second portion 124 further comprises a rounded lip 126. In an embodiment, the leaflet further comprises an elbow 128 between the first portion 122 and the second portion 124. In an embodiment, the elbow 128 between the first portion 122 and second portion 124 comprises an angle less than 20 degrees. In an embodiment, the elbow 128 between the first portion 122 and second portion 124 comprises an angle less than 30 degrees. In an embodiment, the elbow 128 between the first portion 122 and second portion 124 comprises an angle less than 40 degrees. In an embodiment, the elbow 128 between the first portion 122 and second portion 124 comprises an angle less than 50 degrees. In an embodiment, the elbow 128 between the first portion 122 and second portion 124 comprises an angle less than 60 degrees. In an embodiment, the elbow 128 between the first portion 122 and second portion 124 comprises an angle less than 70 degrees. In an embodiment, the elbow 128 between the first portion 122 and second portion 124 comprises an angle less than 80 degrees. In an embodiment, the elbow 128 between the first portion 122 and second portion 124 comprises an angle less than 90 degrees. In an embodiment, the elbow 128 between the first portion 122 and second portion 124 comprises an angle less than 100 degrees. In an embodiment, the elbow 128 between the first portion 122 and second portion 124 comprises an angle less than 110 degrees. In an embodiment, the elbow 128 between the first portion 122 and second portion 124 comprises an angle less than 120 degrees.

In an embodiment, a torque limiting surgical screw driver may limit the torque that may be applied in both directions of rotation of the torque limiting surgical screw driver's handle. That is, in an embodiment, a torque limiting surgical screw driver may limit the amount of torque that may be applied by a user when the torque limiting surgical screw driver handle is turned both in the clockwise as well as counterclockwise direction. In an embodiment, a torque limiting surgical screw driver limits the torque applied by a user to a first torque in the clockwise direction and a second torque in the counter clockwise direction. In an embodiment, a torque applied to a screw being driven into a bone by a torque limiting surgical screw driver is limited to a first torque, and a torque applied to a screw being pulled out (unscrewed) from a bone is limited to a second torque. In an embodiment, the torque limited by a torque limiting surgical screw driver may be limited in both the clockwise and counter clockwise direction when two torque limiting elements on either the handle or driver shaft are configured to engage with a single torque limiting element on either the handle or driver shaft. For example, in an embodiment, a first and second torque limiting element are positioned on a handle as described herein and a third torque limiting element is positioned on a driver shaft. In this embodiment, the third torque limiting element on the driver shaft is positioned between the first and second torque limiting elements on the handle when the handle is coupled with the driver shaft. In this embodiment, when the handle is turned in a clockwise direction the third torque limiting element on the driver shaft engages the second torque limiting element on the handle in a manner as described herein and when the handle is turned in a counter clockwise direction the third torque limiting element on the driver shaft engages the first torque limiting element as described herein. In an embodiment, the first and second torque limiting elements on the handle are identical such that they will resist disengagement from the third torque limiting element on the handle to the same extent for both clockwise and counter-clockwise rotation. In an embodiment, the first and second torque limiting elements on the handle are different and as such are configured to resist disengagement from the third torque limiting element on the handle to the same extent for both clockwise and counter-clockwise rotation. In an embodiment, a single torque limiting element on the handle is positioned between two torque limiting elements on the driver shaft when the handle is coupled with driver shaft. In an embodiment, one or more pairs of torque limiting engagers on either the handle or the driver shaft are respectively engaged with a single torque limiting engager on either the handle or the driver shaft when the handle is coupled with the driver shaft as described herein.

Figure 2:
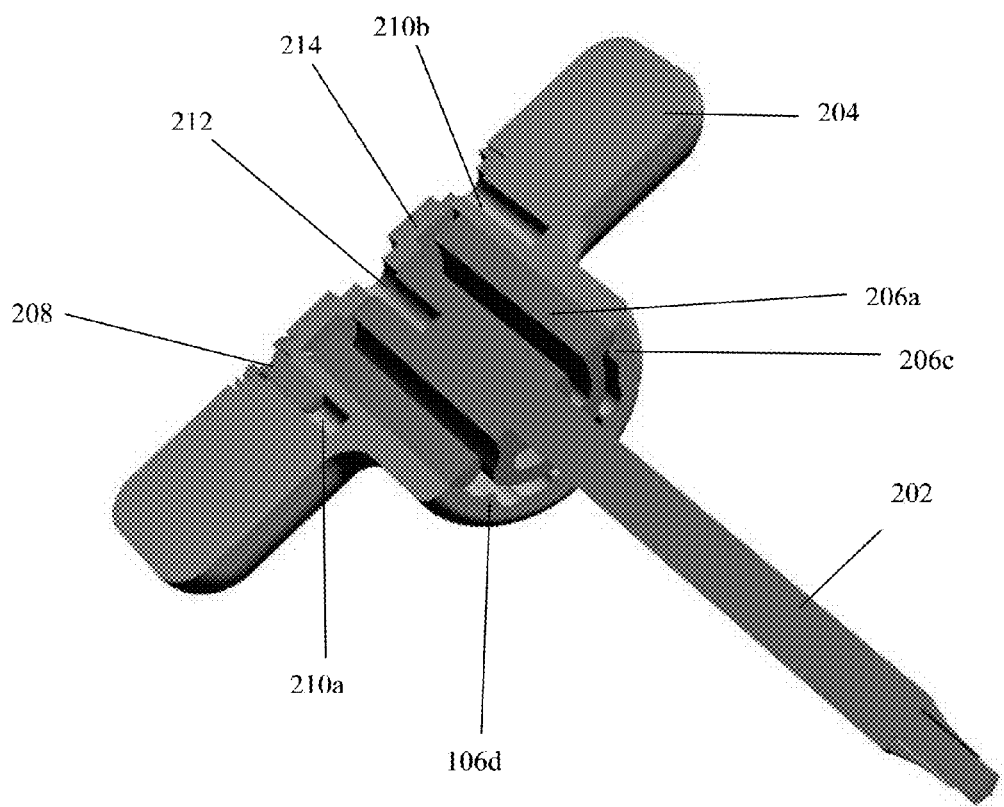
FIG. 2 shows a cross-sectional view of an embodiment of a torque limiting surgical screw driver as described herein.

FIG. 2 shows a cross-sectional view of an embodiment of a torque limiting surgical screw driver. In this embodiment, a central screw saddle 212 is configured to receive either a screw or pin that will couple a handle 204 to a driver shaft 202. In an embodiment, when a screw or pin is positioned within central screw saddle, the handle 204 is rotatably coupled to the driver shaft 202, such that when an sufficient torque is applied to a handle 204 and driver shaft 202 is held in place, the handle 204 may rotate about the driver shaft 202. Lateral screw saddles 210a and 210b are configured to receive a screw 208 or rod that secures a cover plate 214 to the torque limiting surgical screw driver. Torque limiting element 206a is shown in cross-section. In an embodiment, torque limiting element 206a extends along the length of the handle 204. Torque limiting element 206a is shown engaged with torque limiting element 206c. In an embodiment, a torque limiting surgical screw driver comprises more torque limiting elements on the handle 204 than on the driver shaft 202 such that not all of the torque limiting elements on the handle 204 are engaged to a torque limiting element on the driver shaft at any time. For example, FIG. 2 shows torque limiting element 206c on the handle 204 is engaged with a torque limiting element 206a on a driver shaft 202, and torque limiting element 206b is not engaged to any torque limiting elements from the driver shaft 202.

Figure 3:
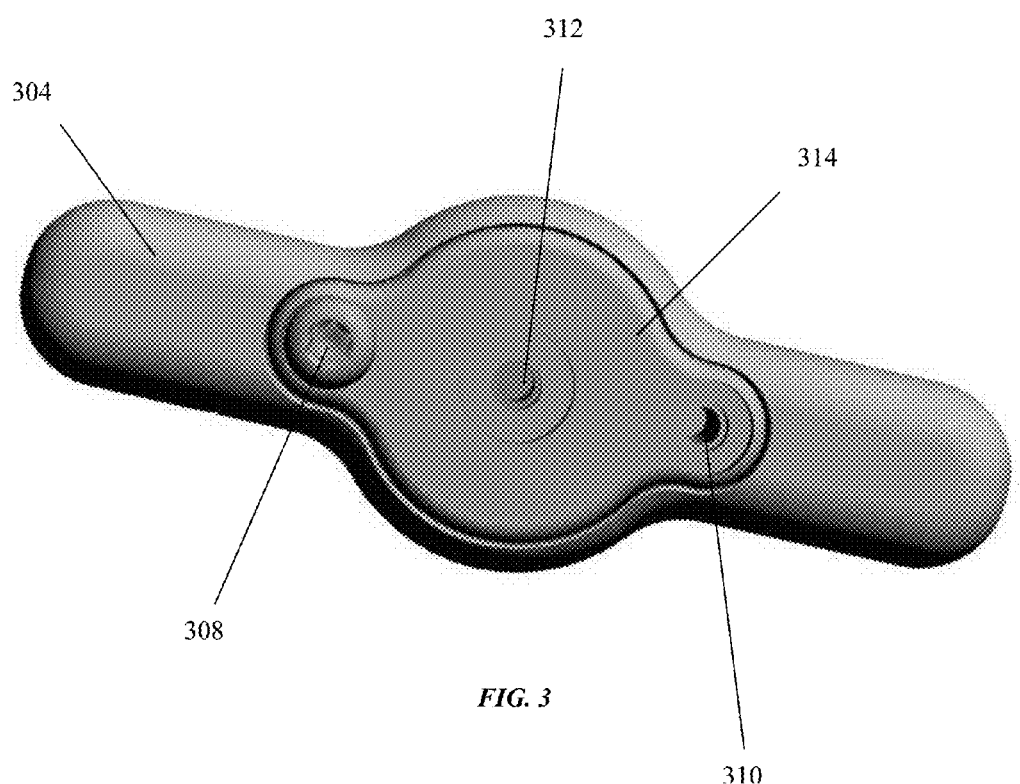
FIG. 3 shows a top view of an embodiment of a torque limiting surgical screw driver as described herein.

FIG. 3 shows a top view of an embodiment of a torque limiting surgical screw driver. In an embodiment, a torque limiting surgical screw driver includes a screw plate 314, which is positioned on top of the handle 304 and which may be secured with a screw 308 that is positioned in a lateral saddle not shown, by central screw (not shown) that is positioned in central screw saddle 312, and a lateral screw (not shown) that is positioned in lateral saddle 310.

Figure 4:
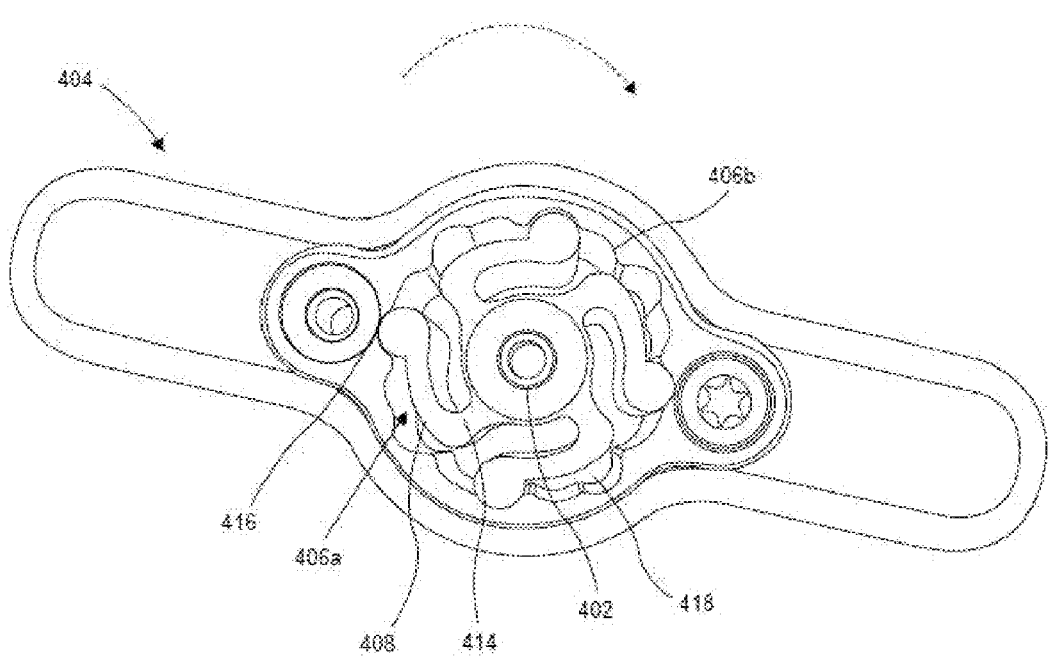
FIG. 4 shows a cross-sectional view of an embodiment of a torque limiting surgical screw driver as described herein.

FIG. 4 shows a cross-sectional view of an embodiment of a torque limiting surgical screw driver. In an embodiment, a torque limiting element 406a on a driver shaft 402 comprises a top section 416 that is configured to engage a torque limiting element on a handle 406b, an elbow 408 as described herein, and a bottom portion 414 that is configured to couple with or attach to a driver shaft 402. In an embodiment, a handle 404 comprises a groove 418 configured to receive the top section 416 of the torque limiting element 406a. The dashed line indicates the direction of rotation applied to the handle when the torque limiting surgical screw driver is operated.

Figure 5A:
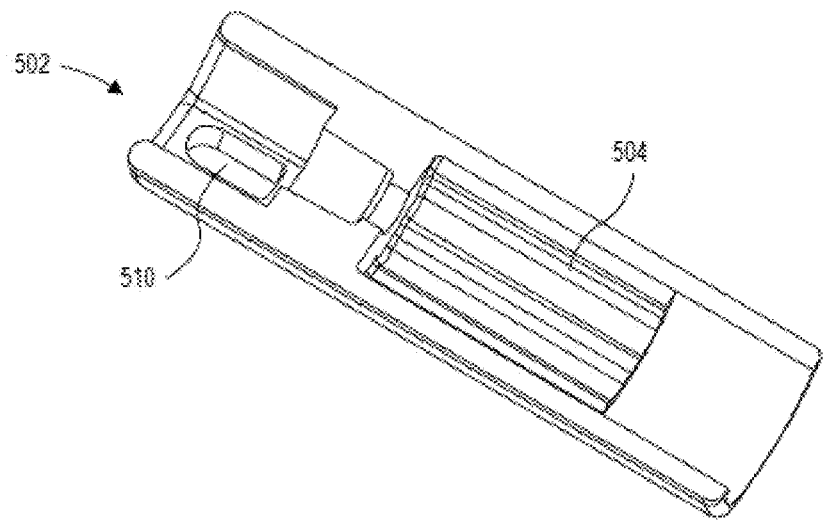
FIGS. 5A-5B show cross-sectional views of an embodiment handle as described herein.
Figure 5B:
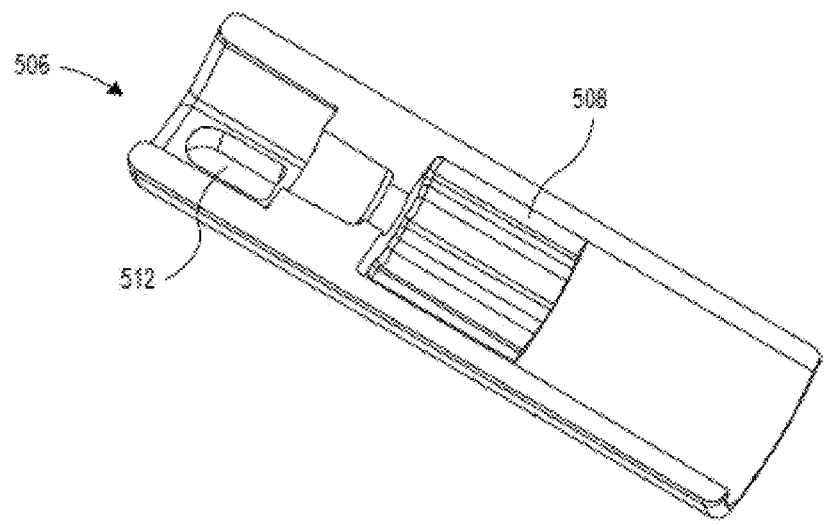

FIGS. 5A-5B show cross-sectional views of a handle 502 and 506. In an embodiment, a torque limiting surgical screw driver may be manufactured to a set torque limit by, for example, setting the length of a torque limiting elements along the inside of the handle 504 (in FIG. 5A) and 508 (in FIG. 5B). In an embodiment, torque limiting elements along the inside of the handle 504 and 508 may be configured to engage one or more leaflets on a torque limiting unit that is coupled with the driver shaft, as described herein. Where the torque limiting elements on the torque limiting unit (e.g. leaflets) remain the same length, varying the set torque at which the torque limiting elements on the torque limiting unit will disengage from the corresponding torque limiting elements on the inside of the handle 504 and 508 may be achieved during the manufacture of the device by varying the length of the torque limiting elements on the inside of the handle 504 and 508. Typically, relatively longer torque limiting elements on the inside of the handle 504, as shown in FIG. 5A, will require a relatively greater amount of torque to disengage the respective torque limiting elements on the torque limiting unit as compared to the relatively shorter torque limiting elements on the inside of the handle 508, as shown in FIG. 5B. Typically, relatively shorter torque limiting elements 508, as shown in FIG. 5B, will require a relatively smaller amount of torque to disengage the respective torque limiting elements on the torque limiting unit 508 as compared to the longer torque limiting elements on the inside of the handle 504, as shown in FIG. 5A. In an embodiment, the length of the torque limiting elements on the torque limiting unit are modified during manufacture so as to determine the amount of torque that will cause the torque limiting elements on the torque limiting unit to disengage from the torque limiting elements on the inside of the handle 504 and 508. In an embodiment, both the length of the torque limiting unit and the lengths of the torque limiting elements on the handle 504 and 508 may both be modified during manufacture to determine a desired torque at which the respective elements disengage. Also shown in FIGS. 5A and 5B is an embodiment of the torque limiting surgical screw driver described herein and further comprises a snap connector 510 and 512 to facilitate the connecting of a handle arm (not shown) that snap fits with the snap fit connector 510 and 512. In an embodiment, a snap-fit connector 510 and 512 comprises an opening in the handle.

FIGS. 6A-6B show a cross-section of an embodiment of the torque limiting surgical screw driver 602 and 606 described herein. Specifically, FIGS. 6A-6B show how a torque limiting unit 604 and 608 comprising one or more torque limiting elements and coupled with the driver shaft engages with the torque limiting elements on the handle 610 and 616. As shown, the torque limiting elements on the handle 610 shown in FIG. 6A are longer than the torque limiting elements on the handle 616 shown in FIG. 6B, thus, assuming the torque limiting units were the same length, the torque required to disengage the respective torque limiting elements is greater in FIG. 6A than in FIG. 6B. FIGS. 6A-6B also show an embodiment in which a single handle arm 612 and 614 is coupled with a connector such as, for example, a snap fit connector on the handle (not shown). In an embodiment, the handle of the torque limiting surgical screw driver is configured to couple with a handle arm 612 and 614 that aids a user in applying torque. In an embodiment, the handle is coupled to the handle arm 612 and 614 by a user. In an embodiment, a handle arm 612 and 614 reversibly couples with a handle.

Figure 7A:
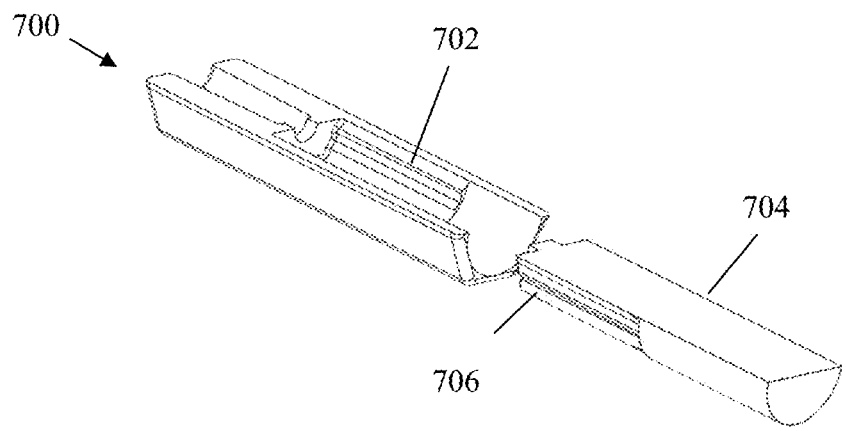
FIGS. 7A-7B show cross-sectional views of an embodiment of a handle together with a cross sectional view of an embodiment of a moveable mold as described herein.
Figure 7B:
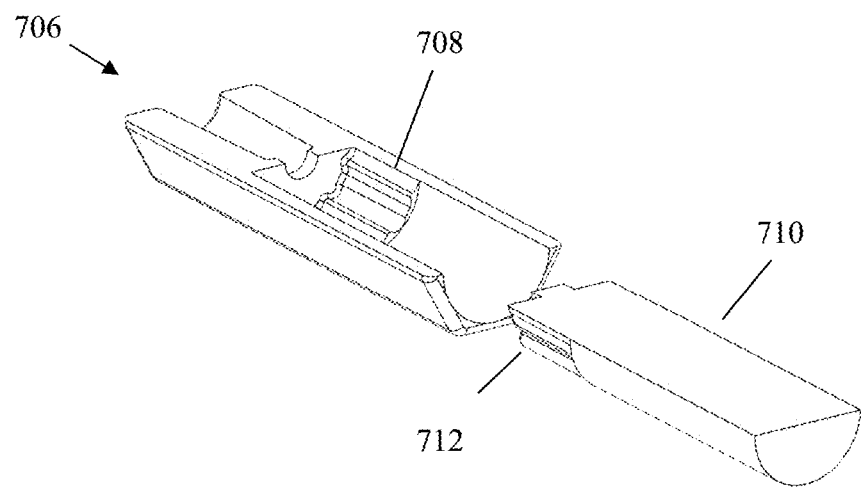

FIGS. 7A-7B show cross-sectional views of a handle 700 and 706 together with a cross sectional view of a moveable mold 704 and 710. In an embodiment, the torque limiting surgical screw driver described herein comprises components that are injection molded. In an embodiment, the torque limiting elements on the inside of the handle 702 and 708 are molded by the projections and grooves 706 and 712 on a moveable mold 704 and 710. In this embodiment, the handle 702 and 706 is formed as a hollow essentially cylindrical shape (shown in cross-section in FIGS. 7A-7B) and a moveable mold 704 and 720, which too is essentially cylindrically shaped (shown in cross-section in FIGS. 7A-7B), slides into the handle 700 and 706 during manufacture to mold the torque limiting elements on the inside of the handle 702 and 708. The projections and grooves 706 on the moveable mold 704 shown in FIG. 7A are longer than the projections and grooves 712 on the moveable mold 710 shown in FIG. 7B. Therefore, the torque limiting elements formed on the inside of handle 702, shown in FIG. 7A, are longer than the torque limiting elements on the inside of the handle 708, shown in FIG. 7B. In this embodiment, the torque that is required to disengage the respective torque limiting elements on the inside of the handle 702 and 708 and the torque limiting elements on or coupled with the driver shaft is determined by the length of the projections and grooves 706 and 712 on the moveable 704 and 710.

Figure 8A:
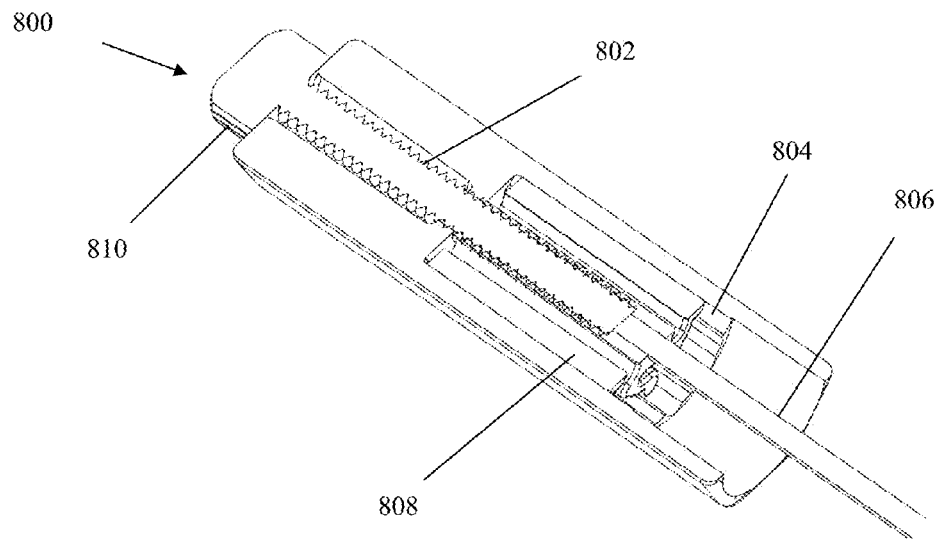
FIGS. 8A-8B show cross-sectional views of an embodiment of a user adjustable torque limiting surgical screw driver as described herein.
Figure 8B:
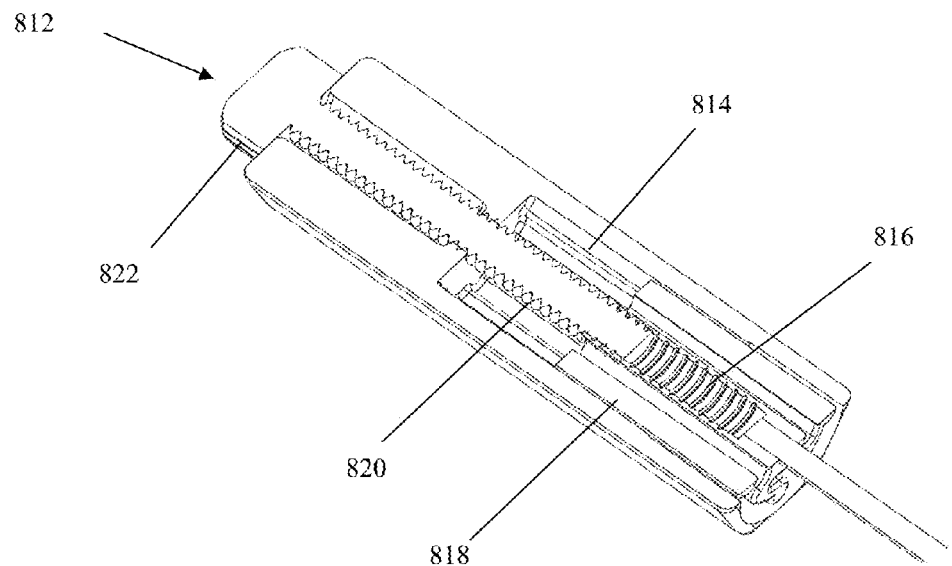

FIGS. 8A-8B show cross-sectional views of a user adjustable torque limiting surgical screw driver. In an embodiment, a user adjustable torque limiting surgical screw driver comprises a control knob 810 and 822, wherein the control knob 810 and 822 is configured to allow a user to adjust a torque limit at which the torque limiting elements on the torque limiting unit 808 will disengage from the torque limiting units on the inside of the handle 804 and 814. In an embodiment, an adjustment knob 810 and 822 is functionally connected to a threaded rod 802 and 822. In an embodiment, the threaded rod 802 and 820 threadably couples with threading on the inside 816 of the torque limiting unit 818 as shown in FIG. 8B. In this embodiment, as a user rotates the adjustment knob 810 and 822, the threadably coupled torque limiting unit 808 and 818 is either advanced or withdrawn relative to the torque limiting elements on the inside of the handle 804 and 814 depending on the direction that the adjustment knob 810 and 820 is rotated relative to the threading. Typically, as the torque limiting unit 808 and 820 is advanced down the length of the axis due to the user rotating the adjustment knob 810 and 822, less of the surface of the torque limiting elements on the torque limiting unit 808 and 818 will be in contact (i.e. engaged) with the torque limiting elements on the inside of the handle 808 and 818. When less of the surface of the torque limiting elements on the torque limiting unit 808 and 818 are in contact with the torque limiting elements on the inside of the handle 804 and 814, a smaller amount of torque is required to cause the torque limiting elements on the torque limiting unit 808 and 818 and the torque limiting elements on the inside of the handle 804 and 814 to disengage. FIG. 8B shows an embodiment in which the torque limiting unit 818 has been advanced along the length of the handle so that a smaller amount of torque is required to cause the torque limiting elements on the torque limiting unit 808 and 818 and the torque limiting elements on the inside of the handle 804 and 814 to disengage relative to the embodiment shown in FIG. 8A. FIG. 8A shows an embodiment in which the torque limiting unit 818 has been withdrawn into the handle so that the entire surface of the torque limiting elements on the torque liming unit 808 and 818, that are configured to engage with the torque limiting elements on the inside of the handle 804 and 814, are positioned to engage with the torque limiting elements on the inside of the handle 804 and 814. In the embodiment shown in FIG. 8A, a larger amount of torque is required to cause the torque limiting elements on the torque limiting unit 804 and 814 and the torque limiting elements on the inside of the handle 804 and 818 to disengage relative to the embodiment shown in FIG. 8B.

While preferred embodiments of the systems, devices, and methods described herein have been shown and described herein, it will be obvious to those skilled in the art that such embodiments are provided by way of example only. Numerous variations, changes, and substitutions will now occur to those skilled in the art without departing from the subject matter described herein. It should be understood that various alternatives to the embodiments of the systems, devices, and methods described herein may be employed in practicing the systems, devices, and methods described herein. It is intended that the following claims define the scope of the invention and that methods and structures within the scope of these claims and their equivalents be covered thereby.

What is claimed is:

1. A torque limiting surgical screw driver, comprising
    a driver shaft having a proximal end and a distal end, wherein the proximal end comprises a first torque limiting element, and wherein the distal end is configured to engage with a screw head used in a surgical procedure; and
    a handle coupled with the proximal end of the driver shaft, wherein the handle comprises
        a first opening configured to receive the proximal end of the driver shaft;
        a hollow interior continuous with the opening, and
        a second torque limiting element within the hollow interior positioned to engage the first torque limiting element on the proximal end of the driver shaft;
        a track positioned on the hollow interior of the handle and contiguous with the second torque limiting element;
    wherein the first torque limiting element and the second torque limiting element are configured to disengage from each other when a torque above a first threshold torque is applied to the handle when the handle is rotated in a clockwise direction; and
    wherein the first torque limiting element comprises a leaflet comprising a first and a second portion, wherein the first portion and the second portion are joined to form an elbow in the leaflet;
    wherein the second portion of the leaflet comprises a rounded lip; and
    wherein the rounded lip is positioned to contact the track on the hollow interior of handle when the first torque limiting element and the second torque limiting element disengage and the handle is rotated in a clockwise direction.

2. The torque limiting surgical screw driver of claim 1, wherein the driver shaft has a length of about 30 cm.

3. The torque limiting surgical screw driver of claim 1, wherein the elbow forms an angle of 90 degrees or less.

4. The torque limiting surgical screw driver of claim 1, wherein the handle is configured to reversibly couple with the driver shaft via a coupling mechanism.

5. The torque limiting surgical screw driver of claim 4, wherein the coupling mechanism comprises one or more threaded components.

6. The torque limiting surgical screw driver of claim 4, wherein one or more of the driver shaft and the handle are disposable.

7. The torque limiting surgical screw driver of claim 1, wherein the second torque limiting element is positioned so as to engage the first torque limiting element in a side by side fashion when the driver shaft is coupled with the handle.

8. The torque limiting surgical screw driver of claim 1, wherein the first torque limiting element is configured to bend in response to a pressure applied to the first torque limiting element by the second torque limiting element when the torque above the first threshold torque is applied to the handle causing the first torque limiting element to disengage from the second torque limiting element.

9. The torque limiting surgical screw driver of claim 1, wherein the first threshold torque comprises 90 inch pounds of torque.

10. The torque limiting surgical screw driver of claim 1, wherein the handle comprises a third torque limiting element within the hollow interior, and wherein the first torque limiting element on the driver shaft is positioned between the second and third torque limiting elements when the handle is coupled with the driver shaft.

11. The torque limiting surgical screw driver of claim 10, wherein the first torque limiting element and the third torque limiting elements are configured to disengage from each other when a torque above a second threshold torque is applied to the handle when the handle is rotated in a counter-clockwise direction.

12. The torque limiting surgical screw driver of claim 1, wherein the handle further comprises a snap-fit connector for forming a snap-fit connection to a handle arm, and wherein the snap-fit connector comprises a second opening in the handle.

13. The torque limiting surgical screw driver of claim 1, comprising at least two second torque limiting elements.

* * * * *